(12) United States Patent
Verser et al.

(10) Patent No.: US 8,236,534 B2
(45) Date of Patent: *Aug. 7, 2012

(54) PROCESS FOR PRODUCING ETHANOL

(75) Inventors: Dan Verser, Menlo Park, CA (US);
Timothy J. Eggeman, Englewood, CO (US)

(73) Assignee: Zeachem, Inc., Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/101,900

(22) Filed: May 5, 2011

(65) Prior Publication Data

US 2011/0275127 A1    Nov. 10, 2011

Related U.S. Application Data

(60) Continuation of application No. 12/693,533, filed on Jan. 26, 2010, now Pat. No. 7,964,379, which is a continuation of application No. 12/051,668, filed on Mar. 19, 2008, now Pat. No. 7,682,812, which is a continuation of application No. 11/172,376, filed on Jun. 29, 2005, now Pat. No. 7,351,559, which is a division of application No. 10/310,552, filed on Dec. 4, 2002, now Pat. No. 6,927,048, which is a continuation of application No. 09/720,930, filed as application No. PCT/US00/06498 on Mar. 10, 2000, now Pat. No. 6,509,180.

(60) Provisional application No. 60/124,276, filed on Mar. 11, 1999.

(51) Int. Cl.
| C12P 7/62 | (2006.01) |
| C12P 7/56 | (2006.01) |
| C12P 7/54 | (2006.01) |
| C12P 7/06 | (2006.01) |
| C12N 1/20 | (2006.01) |
| C07C 51/42 | (2006.01) |
| C07C 53/21 | (2006.01) |

(52) U.S. Cl. ........ 435/135; 435/139; 435/140; 435/161; 435/162; 435/163; 435/252.7; 562/600; 562/606; 562/608

(58) Field of Classification Search .................. 435/135, 435/140, 252.7, 139, 161, 162, 163; 562/600, 562/606, 608

See application file for complete search history.

(56) References Cited

U.S. PATENT DOCUMENTS

| 1,421,605 A | 7/1922 | Steffens |
| 2,079,414 A | 5/1937 | Lazier |
| 2,565,487 A | 8/1951 | Filachione et al. |
| 2,782,243 A | 2/1957 | Hess et al. |
| 3,678,118 A | 7/1972 | Frampton et al. |
| 3,686,334 A | 8/1972 | Britton |
| 3,769,329 A | 10/1973 | Paulik et al. |
| 3,878,261 A | 4/1975 | Gardner |
| 3,956,482 A | 5/1976 | Hahn et al. |
| 4,055,590 A | 10/1977 | Gruber et al. |
| 4,100,189 A | 7/1978 | Mercier |
| 4,113,662 A | 9/1978 | Wall |
| 4,134,926 A | 1/1979 | Tsao et al. |
| 4,140,799 A | 2/1979 | Nagodawithana et al. |
| 4,206,036 A | 6/1980 | Takeuchi et al. |
| 4,275,234 A | 6/1981 | Baniel et al. |
| 4,282,323 A | 8/1981 | Yates |
| 4,353,784 A | 10/1982 | Koga et al. |
| 4,359,404 A | 11/1982 | Grey et al. |
| 4,370,507 A | 1/1983 | Hargis et al. |
| 4,371,619 A | 2/1983 | Schwartz et al. |
| 4,379,028 A | 4/1983 | Berg et al. |
| 4,405,717 A | 9/1983 | Urbas |
| 4,421,939 A | 12/1983 | Kiff et al. |
| 4,431,838 A | 2/1984 | Feldman et al. |
| 4,435,595 A | 3/1984 | Agreda et al. |
| 4,444,881 A | 4/1984 | Urbas |
| 4,454,358 A | 6/1984 | Kummer et al. |
| 4,497,967 A | 2/1985 | Wan |
| 4,506,012 A | 3/1985 | Reed |
| 4,513,084 A | 4/1985 | Keller, Jr. et al. |
| 4,517,391 A | 5/1985 | Ludwig et al. |
| 4,568,644 A | 2/1986 | Wang et al. |
| 4,569,726 A | 2/1986 | Berg et al. |
| 4,636,467 A | 1/1987 | Chynoweth |
| 4,649,112 A | 3/1987 | Datta et al. |
| 4,652,526 A | 3/1987 | Hsu |
| 4,687,668 A | 8/1987 | Ghommidh et al. |
| 4,690,912 A | 9/1987 | Paulik et al. |
| 4,698,303 A | 10/1987 | Bailey et al. |
| 4,771,001 A | 9/1988 | Bailey et al. |
| 4,808,526 A | 2/1989 | Lawford |
| 4,830,963 A | 5/1989 | Brumm et al. |
| 4,851,344 A | 7/1989 | Simon et al. |
| 4,876,196 A | 10/1989 | Salzbrunn et al. |

(Continued)

FOREIGN PATENT DOCUMENTS

GB    933714    8/1963

(Continued)

OTHER PUBLICATIONS

U.S. Appl. No. 12/511,526, filed Jul. 29, 2009, Verser et al.

(Continued)

*Primary Examiner* — Herbert J Lilling
(74) *Attorney, Agent, or Firm* — Sheridan Ross P.C.

(57) ABSTRACT

A process for producing ethanol including a combination of biochemical and synthetic conversions results in high yield ethanol production with concurrent production of high value coproducts. An acetic acid intermediate is produced from carbohydrates, such as corn, using enzymatic milling and fermentation steps, followed by conversion of the acetic acid into ethanol using esterification and hydrogenation reactions. Coproducts can include corn oil, and high protein animal feed containing the biomass produced in the fermentation.

20 Claims, 4 Drawing Sheets

U.S. PATENT DOCUMENTS

| | | | |
|---|---|---|---|
| 4,935,360 | A | 6/1990 | Klemps et al. |
| 4,939,294 | A | 7/1990 | Agreda et al. |
| 4,980,164 | A | 12/1990 | Manfredi et al. |
| 5,028,539 | A | 7/1991 | Ingram et al. |
| 5,068,188 | A | 11/1991 | Wise et al. |
| 5,071,754 | A | 12/1991 | Walkup et al. |
| 5,093,121 | A | 3/1992 | Kvanta et al. |
| 5,137,818 | A | 8/1992 | Harder et al. |
| 5,162,214 | A | 11/1992 | Hubred |
| 5,173,429 | A | 12/1992 | Gaddy et al. |
| 5,182,199 | A | 1/1993 | Hartley |
| 5,210,296 | A | 5/1993 | Cockrem et al. |
| 5,231,017 | A | 7/1993 | Lantero et al. |
| 5,254,465 | A | 10/1993 | Wise |
| 5,308,619 | A | 5/1994 | Schmeider et al. |
| 5,316,928 | A | 5/1994 | Flickinger et al. |
| 5,412,126 | A | 5/1995 | King et al. |
| 5,424,202 | A | 6/1995 | Ingram et al. |
| 5,453,365 | A | 9/1995 | Sterzel et al. |
| 5,510,526 | A | 4/1996 | Baniel et al. |
| 5,563,069 | A | 10/1996 | Yang |
| 5,591,877 | A | 1/1997 | Obermeier et al. |
| 5,599,976 | A | 2/1997 | Scates et al. |
| 5,620,877 | A | 4/1997 | Farone et al. |
| 5,635,368 | A | 6/1997 | Lommi et al. |
| 5,681,728 | A | 10/1997 | Miao |
| 5,693,296 | A | 12/1997 | Holtzapple et al. |
| 5,723,639 | A | 3/1998 | Datta et al. |
| 5,750,732 | A | 5/1998 | Verser et al. |
| 5,753,474 | A | 5/1998 | Ramey et al. |
| 5,766,439 | A | 6/1998 | Eyal et al. |
| 5,773,653 | A | 6/1998 | Baniel |
| 5,780,276 | A | 7/1998 | Baniel |
| 5,865,898 | A | 2/1999 | Holtzapple et al. |
| 5,874,263 | A | 2/1999 | Holtzapple et al. |
| 5,892,102 | A | 4/1999 | Mikami et al. |
| 5,969,189 | A | 10/1999 | Holtzapple et al. |
| 5,986,133 | A | 11/1999 | Holtzapple et al. |
| 6,043,392 | A | 3/2000 | Holtzapple et al. |
| 6,136,577 | A | 10/2000 | Gaddy |
| 6,160,173 | A | 12/2000 | Eyal et al. |
| 6,262,313 | B1 | 7/2001 | Holtzapple et al. |
| 6,284,904 | B1 | 9/2001 | Ponnampalam |
| 6,368,819 | B1 | 4/2002 | Gaddy et al. |
| 6,395,926 | B1 | 5/2002 | Holtzapple et al. |
| 6,478,965 | B1 | 11/2002 | Holtzapple et al. |
| 6,509,180 | B1 | 1/2003 | Verser et al. |
| 6,703,227 | B2 | 3/2004 | Jakel et al. |
| 6,740,508 | B2 | 5/2004 | Ulrich et al. |
| 6,926,810 | B2 | 8/2005 | Cockrem et al. |
| 6,927,048 | B2 | 8/2005 | Verser et al. |
| 7,074,603 | B2 | 7/2006 | Verser et al. |
| 7,309,602 | B2 | 12/2007 | David |
| 7,351,559 | B2 | 4/2008 | Verser et al. |
| 7,507,562 | B2 | 3/2009 | Verser et al. |
| 7,601,865 | B2 | 10/2009 | Verser et al. |
| 7,682,812 | B2 | 3/2010 | Verser et al. |
| 7,888,082 | B2 | 2/2011 | Verser et al. |
| 7,964,379 | B2 | 6/2011 | Verser et al. |
| 2004/0168960 | A1 | 9/2004 | Holtzapple et al. |
| 2004/0171136 | A1 | 9/2004 | Holtzapple et al. |
| 2005/0112739 | A1 | 5/2005 | Golubkov |
| 2006/0024801 | A1 | 2/2006 | Holtzapple et al. |
| 2006/0188980 | A1 | 8/2006 | Holtzapple et al. |
| 2006/0222585 | A1 | 10/2006 | Verser et al. |
| 2007/0014895 | A1 | 1/2007 | Holtzapple et al. |
| 2008/0102502 | A1 | 5/2008 | Foody et al. |
| 2008/0176301 | A1 | 7/2008 | Granda et al. |
| 2008/0193989 | A1 | 8/2008 | Verser et al. |
| 2008/0248540 | A1 | 10/2008 | Yang |
| 2008/0280338 | A1 | 11/2008 | Hall et al. |
| 2009/0203098 | A1 | 8/2009 | Verser |
| 2009/0281354 | A1 | 11/2009 | Mariansky et al. |
| 2010/0120104 | A1 | 5/2010 | Reed |
| 2010/0187472 | A1 | 7/2010 | Verser et al. |

FOREIGN PATENT DOCUMENTS

| | | |
|---|---|---|
| JP | S57-140732 | 8/1982 |
| JP | S59-29633 | 2/1984 |
| JP | S61-007222 | 1/1986 |
| JP | S62-171689 | 7/1987 |
| JP | H08-503375 | 4/1996 |
| JP | 11-503514 | 3/1999 |
| WO | WO 82/03854 | 11/1982 |
| WO | WO 83/03409 | 10/1983 |
| WO | WO 93/00440 | 1/1993 |
| WO | WO 99/00352 | 1/1999 |
| WO | WO 99/00512 | 1/1999 |
| WO | WO 00/53791 | 9/2000 |
| WO | WO 2004/041995 | 5/2004 |
| WO | WO 2006/007406 | 1/2006 |
| WO | WO 2007/009085 | 1/2007 |
| WO | WO 2008/070561 | 6/2008 |

OTHER PUBLICATIONS

Agreda et al., "High Purity Methyl Acetate by Reactive Distillation," Chem. Eng. Prog., Feb. 1990, pp. 40-46.

Balasubramanian et al., "Fermentation of Xylose into Acetic Acid by *Clostridium thermoaceticum*," Appl Biochem and Biotech, 2001, vol. 91-93, pp. 367-376.

Ben-Bassat et al., "Ethanol production by thermophilic bacteria: metabolic control of end product formation in *Thermoanaerobium brockii*," J Bacteriol, Apr. 1981, vol. 146(1), pp. 192-199.

Bock et al., "Development of a Low-Cost, Industrially Suitable Medium for the Production of Acetic Acid From *Clostridum Thermoaceticum*," Biotechnol. Appl. Biochem., 1997, vol. 25, pp. 117-125.

Borden et al., "Simultaneous Saccharification and Fermentation of Cellulosic Biomass to Acetic Acid," Appl Biochem and Biotech, 2000, vol. 84-86, pp. 963-970.

Brownell et al., "Bioconversion of Acid-Hydrolyzed Poplar Hemicellulose to Acetic Acid by *Clostridium thermoaceticum*," J. Ind. Microbiol, 1991, vol. 7, pp. 1-6.

Busche et al., "Recovery of Acetic Acid From Dilute Acetate Solution," Biotechnol. Bioeng. Symp., 1982, No. 12, pp. 249-262.

Busche, Robert M., "Recovering Chemical Products from Dilute Fermentation Broths," Biotechnology and Bioengineering Symp, 1983, No. 13, pp. 597-615.

Buschhorn et al., "Production and utilization of ethanol by the homoacetogen *Acetobacterium woodii*," Appl. Environ. Microbiol., 1989, vol. 55, pp. 1835-1840.

Chang et al., "Fundamental Factors Affecting Biomass Enzymatic Reactivity," Appl. Biochem. and Biotech., 2000, vol. 84-86, pp. 5-37.

Cooper et al., "A Renewed Boost for Ethanol," Chemical Engineering, Feb. 1999, pp. 35-39.

Daniel et al., "Utilization of methoxylated aromatic compounds by the acetogen *Clostridium thermoaceticum*: expression and specificity of the co-dependent O-demethylating activity," Biochem Biophys Res Commun., Oct. 1991, vol. 180(1), pp. 416-422.

Drake, "Acetogenesis, Acetogenic Bacteria, and the Acetyl-CoA 'Wood/Ljungdahl' Pathway: Past and Current Perspectives," Chapter 1 of Acetogenesis, 1994, Chapman and Hall, Inc., New York, NY, pp. 3-60.

Drake, Acetogenesis, Figure 12.2, 1994, Chapman Hall, New York, p. 343.

Drake et al., "Old Acetogens, New Light," Ann. NY Acad. Sci., 2008, vol. 1125, pp. 100-128.

Eggeman et al., "Recovery of Organic Acids from Fermentation Broths," Applied Biochemistry and Biotechnology, Mar. 1, 2005, vol. 122, pp. 605-618.

Eggeman et al., "The importance of utility systems in today's biorefineries and a vision for tomorrow," Applied Biochemistry and Biotechnology, Mar. 2006, vol. 130(1-3), pp. 361-381.

Filachione et al., "Preparation of Esters by Reaction of Ammonium Salts with Alcohols," Nov. 1951, pp. 5265-5267 [Presented in part at the 116th A.C.S. Meeting held in Atlantic City, N.J., Sep. 1949, and also at the Miniature meeting of the Philadelphia Section of the American Chemical Society held in Philadelphia, PA., in Jan. 1949].

Grohmann et al., "Saccharification of Corn Fibre by Combined Treatment with Dilute Sulphuric Acid and Enzymes," Process Biochem., 1997, vol. 32(5), pp. 405-415.

Gulati et al., "Assessment of Ethanol Production Options for Corn Products," Bioresource Technology 58, 1996, pp. 253-264.

Hull et al., "Composition of Corn Steep Water During Steeping," J. Agric. Food Chem., 1996, vol. 44, pp. 1857-1863.

Husson et al., "Regeneration of Lactic and Succinic Acid-Laden Basic Sorbents by Leaching with a Volatile Base in an Organic Solvent," Ind. Eng. Chem. Res., 1998, vol. 37, pp. 2996-3005.

Karnholz et al., "Tolerance and Metabolic Response of Acetogenic Bacterial Toward Oxygen," Applied and Environmental Microbiology, 2002, vol. 68(2), pp. 1005-1009.

Leathers et al., "Saccharification of Corn Fiber Using Enzymes from Aureobasidium sp. Strain NRRL Y-2311-1," Applied Biochemistry and Biotechnology, 1996, vol. 59, pp. 337-347.

Liden et al., "Two amperometric biosensors as liquid chromatographic detectors for on-line monitoring of carbohydrate consumption and ethanol production in bioprocesses," 8th International Conference on Solid-State Sensors and Actuators, and Eurosensors IX, Stockholm, Sweden, Jun. 1996, vol. 1, pp. 474-477.

Lovitt et al., "Ethanol production by thermophilic bacteria: biochemical basis for ethanol and hydrogen tolerance in *Clostridium thermohydrosulfuricum*," J Bacteriol, Jun. 1988, vol. 170(6), pp. 2809-2815.

Luedeking et al., "A Kinetic Study of the Lactic Acid Fermentation; Batch Process at Controlled PH," J. Biochem. Microbiol. Tech. Eng., 1959, vol. 1(1), pp. 393-412.

Lundie, Jr. et al., "Development of a Minimally Defined Medium for the Acetogen *Clostridium thermoaceticum*," J. of Bacteriology, 1984, vol. 159(2), pp. 700-703, 1984.

Luo et al., "Kinetics of Simultaneous Saccharification and Lactic Acid Fermentation Processes," Biotechnol. Prog., 1997, vol. 13, pp. 762-767.

Matar et al., "Chemistry of Petrochemical Processes," Gulf Publishing Company, 1994, cover, contents, pp. 162-163.

McCoy, "Biomass Ethanol Inches Forward," C&EN, Dec. 7, 1998, pp. 29-32.

Miller et al., "Extraction of Lactic Acid from a Calcium Lactate Solution Using Amine-Containing Solvents and Carbon Dioxide Gas. 1. Experimental Procedures," Industrial & Engineering Chemistry Research, 1996, vol. 35(4), pp. 1156-1162.

Othmer, "Acetic Acid Recovery Methods," Chemical Engineering Progress, Jul. 1958, vol. 54(7), pp. 48-59.

Parekh et al., "Acetate Production from Glucose by *Clostridium Thermoaceticum*," Process Biochemistry International, Aug. 1990, pp. 117-121.

Pöpken, et al., "Reaction Kinetics and Chemical Equilibrium of Homogeneously and Heterogeneously Catalyzed Acetic Acid Esterification with Methanol and Methyl Acetate Hydrolysis," Industrial and Engineering Chemistry Research, Jun. 17, 2000, vol. 39(7), pp. 2601-2611.

Reisinger et al., "Extraction and Sorption of Acetic Acid at pH above pKa to Form Calcium Magnesium Acetate," Ind. Eng. Chem. Res., 1995 vol. 34, pp. 845-852.

Richert et al., "Thermophilic Fermentation to Make Ethanol from Carbohydrate Byproducts," Genetic Engineering News, Oct. 1, 1998, 1 page.

Ricker et al., "Solvent Extraction With Amines for Recovery of Acetic Acid From Dilute Aqueous Industrial Streams," J. Separ. Proc. Technol., 1980, vol. 1(2), pp. 23-30.

Ricker et al., "Solvent Properties of Organic Bases for Extraction of Acetic Acid from Water," Journal of Separation Process Technology, 1979, vol. 1(1), pp. 36-41.

Saha et al., "Recovery of dilute acetic acid through esterification in a reactive distillation column," Catalysis Today, 2000, vol. 60, pp. 147-157.

Savage et al., "Adaptation of the Acetogen *Clostridium thermoautotropicum* to Minimal Medium," Journal of Bacteriology, 1986, vol. 165(1), pp. 315-318.

Schwartz et al., "Acetic Acid Production by *Clostridium thermoaceticum* in pH-Controlled Batch Fermentations at Acidic pH," Applied and Environmental Microbiology, Jun. 1982, vol. 43(6), pp. 1385-1392.

Schwartz et al., "Isolation of a Strain of *Clostridium thermoaceticum* Capable of Growth and Acetic Acid Production at pH 4.5," Applied and Environmental Microbiology, 1982, vol. 43, No. 1, pp. 117-123.

Tamada et al., "Extraction of Carboxylic Acids with Amine Extractants. 3. Effect of Temperature, Water Coextraction, and Process Considerations," Ind. Eng. Chem. Res., 1990, vol. 29, pp. 1333-1338.

Tang et al., "Acetic Acid Production From Whey Lactose by the Co-Culture of *Sterpococcus Lactis* and *Clostridium Formicoaceticum*," Appl. Microbiol. Biotechnol., 1988, vol. 28, pp. 138-143.

Wang et al., "A Novel Route to the Production of Acetic Acid by Fermentation," Biochem. Eng. Renewable Sources, 1978, vol. 74(181), pp. 105-110.

Wardell et al., "Solvent Equilibria for Extraction of Carboxylic Acids from Water," Journal of Chemical and Engineering Data, 1978, vol. 23(2), pp. 144-148.

Witjitra et al., "Effect of Nutrient Sources on Growth and Acetate Production by *Clostridium thermoaceticum*," Enzyme and Microbial Technology, 1996, vol. 19, pp. 322-327.

Xin et al., "Recovery of acetic acid from waste water," Chemical Engineering (China), Oct. 25, 1996, vol. 24(5), pp. 41-44 (including translated abstract).

Xu et al., "Kinetics of Acetic Acid Esterification Over Ion Exchange Catalysts," Canadian J. Chem. Eng., Aug. 1996, vol. 74, pp. 493-500.

Yang et al., "Kinetics and Mathematical Modeling of Homoacetic Fermentation of Lactate by *Clostridium Formicoaceticum*," Biotechnol. Bioeng., 1988, vol. 32, pp. 797-802.

Zeikus et al., "Thermophilic Ethanol Fermentations", Basic Life Sci, 1981, vol. 18, pp. 441-461 (Abstract only).

Zhicai et al., "Esterification—Distillation of Butanol and Acetic Acid," Chemical Engineering Science, 1998, vol. 53(11), pp. 2081-2088.

International Search Report for International (PCT) Patent Application No. PCT/US00/06498, mailed Aug. 14, 2000.

International Preliminary Examination Report for International (PCT) Patent Application No. PCT/US00/06498, mailed Nov. 6, 2000.

Supplementary Partial European Search Report for European Patent Application No. 00917888, dated Feb. 23, 2004.

Supplementary Partial European Search Report for European Patent Application No. 00917888, dated Nov. 20, 2006.

European Search Report for European Patent Application No. 07008768, dated Jul. 3, 2007.

European Search Report and Opinion for European Patent Application No. 08164159.9, dated Dec. 15, 2008.

PROCESS FOR PRODUCING ETHANOL

CROSS REFERENCE TO RELATED APPLICATIONS

The present application is a continuation of U.S. patent application Ser. No. 12/693,533, filed Jan. 26, 2010, now U.S. Pat. No. 7,964,379, which is a continuation of U.S. patent application Ser. No. 12/051,668, filed Mar. 19, 2008, now U.S. Pat. No. 7,682,812, which is a continuation of U.S. patent application Ser. No. 11/172,376, filed Jun. 29, 2005, now U.S. Pat. No. 7,351,559, which is a division of U.S. patent application Ser. No. 10/310,552, filed Dec. 4, 2002, now U.S. Pat. No. 6,927,048, which is a continuation of U.S. patent application Ser. No. 09/720,930, filed Dec. 29, 2000, now U.S. Pat. No. 6,509,180, which is a national stage application of International Application No. PCT/US00/06498, filed Mar. 10, 2000, and which also claims priority to U.S. Provisional Application No. 60/124,276, filed Mar. 11, 1999, each of which is incorporated herein by reference in its entirety.

FIELD OF THE INVENTION

This invention relates to a process for the conversion of carbohydrates from any of a number of sources into ethanol for fuel or chemical use. The invention uses a combination of fermentation and chemical conversion to greatly increase the yield of ethanol from carbohydrates compared to the current art. In addition a high value coproduct may be produced for use in animal feed.

BACKGROUND OF THE INVENTION

Ethanol is a major chemical used in human beverages and food, as an industrial chemical, and as a fuel or a component in fuels, such as reformulated gasoline to reduce emissions from automobiles. This invention relates mainly to the production of ethanol for use as a chemical or fuel.

There are several traditional ethanol processes based on fermentation of carbohydrates. In the most typical process, a carbohydrate derived from grain is hydrolyzed to its component sugars and fermented by yeast to produce ethanol. Carbon dioxide is generated in the process from a fraction of the carbohydrate by the metabolism of the yeast. The generation of carbon dioxide is inherent in the metabolism of the yeast. This production of $CO_2$ by yeast limits the yield of ethanol from yeast to about 52% maximum on a weight basis. This is a major limitation on the economic production of ethanol as the $CO_2$ is of low value and is typically wasted into the atmosphere and may become a burden on the environment.

In addition, yeast have a limited ability to utilize sugars other than glucose. While glucose is the major sugar produced from the hydrolysis of the starch from grains, it is not the only sugar produced in carbohydrates generally. A large research effort has gone into the potential conversion of biomass into ethanol. Biomass in the form of wastes from agriculture such as corn stover, rice straw, manure, etc., and biomass crops such as switch grass or poplar trees, and even municipal wastes such as newspaper can all be converted into ethanol. However a major limitation of these processes is the complexity of the hydrolyzate that results from treatment of the biomass to produce the fermentation medium. The hydrolyzate typically contains glucose, but also large amounts of other sugars such as xylose, which yeast cannot metabolize. This is another potential yield limitation on yeast based ethanol processes.

Research has been directed to the use of organisms other than yeast which in contrast to yeast, do consume many if not most of the sugars derived from the hydrolysis of biomass. Examples include *Zymomonas* sp. bacteria and *E. coli* bacteria which have been genetically engineered to utilize xylose. Thereby the potential range of substrate sugars which can be converted to ethanol has been increased. There is a class of organism that has been proposed for the production of ethanol, typically of the *Clostridium* sp. These thermophiles usually produce both acetic acid and ethanol. However, it is believed that these organisms produce a limited yield of ethanol. It is generally assumed in the literature on ethanol fermentation that this yield limitation is fixed by the biochemical pathway called the Embden-Myerhof pathway by which ethanol is produced in all of the organisms so far proposed for production of ethanol, including the thermophiles.

Thus none of this development has addressed the inherent problem of the yield of ethanol from sugar based on the coproduction by the organisms of $CO_2$.

An important part of the commercial processes for producing ethanol is the production of valuable coproducts mainly for use in animal feed or food. In the corn dry milling process the coproducts include distillers dried grains and solubles (DDG, DDGS). In the corn wet milling process the coproducts include germ, gluten meal and fiber. These coproducts find large markets in the animal feed business. However in both processes to a very large extent, the ingredients in the original grain, that is the oil, protein and fiber fractions, are passed through the processes unchanged in composition, while the carbohydrate fraction is converted largely to ethanol. Therefore the value of these coproducts is based on the inherent composition of the plant components.

There are other chemicals that can be produced by industrial fermentation from carbohydrates besides ethanol. Major examples are acetic acid and lactic acid. Acetic acid is a major food ingredient in the form of vinegar and a major industrial chemical. Vinegar for food use is typically produced from potable ethanol by the action of *Acetobacter* sp. which oxidize ethanol to acetic acid using oxygen from the air.

Major industrial uses for acetic acid are as a solvent, as an intermediate in the synthesis of other chemicals such as vinyl acetate and in the production of cellulose acetate. Major new uses for acetic acid have been proposed such as the production of calcium magnesium acetate (CMA) for use as a road deicer in place of sodium chloride (NaCl). CMA has a much reduced environmental impact compared to NaCl since it is much less corrosive and is biodegradable.

Researchers have proposed the production of industrial grade acetic acid by fermentation from carbohydrates. However no production by fermentation currently exists due to economic factors related mainly to recovering acetic acid from dilute fermentation broths. Acetic acid is typically produced at low concentrations of around 5% or less in water as a fermentation broth. Since acetic acid has a higher boiling point than water, all of the water, about 95% of the broth, must be distilled away from the acetic acid to recover the acid or other more complex processes must be used to recover the acetic acid.

Related to this field of acetic acid production is the use of so called acetogens, a class of bacteria which utilize a unique biochemical pathway to produce acetic acid from sugars with 100% carbon yield. For example, one mole of glucose can be converted to three moles of acetic acid by *Clostridium thermoaceticum*. These bacteria internally convert $CO_2$ into acetate. These bacteria are called homofermentative microorganisms or homoacetogens. They do not convert any of the carbohydrate to $CO_2$ and only produce acetic acid. Examples of homoactogens are disclosed in Drake, H. L. (editor), *Acetogenesis*, Chapman & Hall, 1994, which is incorporated herein by reference in its entirety. In addition these homofermentative organisms typically convert a wide range of sugars into acetic acid, including glucose, xylose, fructose, lactose, and others. Thus they are particularly suited to the fermentation of complex hydrolyzates from biomass. However this line of research has not overcome the economic limitations of the acetic acid fermentation process to make it competitive with the natural gas based route.

Therefore, industrial acetic acid is today made from coal, petroleum or natural gas. The major process is the conversion of natural gas to methanol and the subsequent carbonylation of the methanol using carbon monoxide directly to acetic acid. U.S. Pat. No. 3,769,329 describes this process.

Related to the natural gas route, it has been proposed to produce ethanol from acetic acid by way of synthesis of esters of acetic acid produced in this process, or a related modification, and subsequent hydrogenation of the esters. U.S. Pat. Nos. 4,454,358 and 4,497,967 disclose processes to produce acetic acid from synthesis gas, which is then esterified and hydrogenated to produce ethanol, and are incorporated herein by reference in their entirety. The hydrogenation of esters to produce alcohols is well known. None of these processes are based on the conversion of carbohydrates to ethanol.

There is another class of well known fermentations that have the property of converting carbohydrates at 100% carbon yield, using homofermentative lactic bacteria. These bacteria convert one mole of glucose for example into two moles of lactic acid. The relevance of this is that lactic acid may also be used as the substrate for fermentation to acetic acid by homofermentative acetogens again with 100% carbon yield. Two moles of lactic acid are converted into three moles of acetic acid by *Clostridium formicoaceticum* for example. Prior to the present invention, no one has been known to have devise a process to produce ethanol in high yield from carbohydrates, which is the main objective of this invention.

SUMMARY OF THE INVENTION

In accordance with one embodiment the present invention, carbohydrates are converted to ethanol with very high carbon yield by a combination of fermentation and chemical conversion, thus overcoming the major limitation of known processes for the conversion of carbohydrates to ethanol. The present invention combines several chemical and biochemical steps into a new process with many advantages. The basic process of this invention comprises three steps:

1. Converting a wide range of carbohydrates, with very high carbon yield (>90% potentially) using a homoacetic fermentation (or a combination of homolactic and subsequent homoacetic fermentations) into acetic acid, 2. Recovering, acidifying (if necessary), and converting the acetic acid to an ester (preferably, the ethyl ester using recycled ethanol product), and 3. Hydrogenating the ester, producing ethanol, and regenerating the alcohol moiety of the ester.

The net effect of this process is to convert carbohydrates in very high carbon yield to ethanol. No $CO_2$ is produced from carbohydrates as a byproduct of this process.

Another benefit of the current invention is the production of a higher value byproduct due to the conversion of the plant proteins into bacterial single cell protein. The conversion of the plant protein into single cell bacterial protein increases the concentration of the protein, restructures the protein to have a more valuable composition for animal feed in terms of essential amino acids, for example, and potentially provides other benefits, for example, in milk production.

The conversion of the fiber fraction, and the cellulose and xylan fractions of the grain contributes to the overall yield of ethanol.

While the production of single cell protein and the utilization of fiber are important additional benefits of the invention, the yield factor alone is a major improvement and can be practiced on its own in conjunction with the corn wet milling process, without the production of single cell protein or the utilization of cellulose fiber.

Advantages of the invention over the current state of the art can include one or more of the following:

1. Very high yield of product from raw material with obvious economic benefits compared to known ethanol processes, 2. No production of $CO_2$ from carbohydrate by the process with benefits to the environment, i.e. the much more efficient conversion of renewable resources to ethanol, 3. Inherently wide substrate range for ethanol production, i.e. a wide range of potential biomass sources and their component sugars, and 4. High value byproducts, e.g., single cell protein; restructuring of plant protein, produced with high efficiency.

In one embodiment of the present invention a method to produce ethanol with a very high yield is provided. The method includes the steps of fermenting a medium which contains a carbohydrate source into acetate, acetic acid or mixtures thereof. The acetate, acetic acid, or mixtures thereof are chemically converted to ethanol. Preferably, at least about 60%, more preferably at least about 80% and more preferably at least about 90% of the carbon in the carbohydrate source is converted to ethanol. Essentially none of the carbon in the carbohydrate source is converted into carbon dioxide. However, if hydrogen is produced later in the process by steam reforming, carbon dioxide will be produced at that stage. Preferably, the fermentation medium comprises less than about 20% nitrogen and yields a biomass byproduct which is useful as an animal feed, with preferably at least about 10% by weight biomass product. The carbohydrate source can include any appropriate source such as corn, wheat, biomass, wood, waste paper, manure, cheese whey, molasses, sugar beets or sugar cane. If an agricultural product such as corn is employed, the corn can be ground to produce corn and corn oil for recovery. The carbohydrate source, e.g., corn, can be enzymatically hydrolyzed prior to fermentation. Preferably, the fermentation is conducted using a homofermentative microorganism. The fermentation can be a homoacetic fermentation using an acetogen such as a microorganism of the genus *Clostridium*, e.g., microorganisms of the species *Clostridium thermoaceticum* or *Clostridium formicoaceticum*.

In an embodiment of the present invention, the fermentation includes converting the carbohydrate source into lactic acid, lactate or mixtures thereof by fermentation and subsequently converting the lactic acid, lactate or mixtures thereof into acetic acid, acetate or mixtures thereof by fermentation. The lactic acid fermentation can be a homolactic fermentation accomplished using a microorganism of the genus *Lactobacillus*. Alternatively, the carbohydrate source can be converted into lactic acid, lactate, acetic acid, acetate or mixtures thereof in an initial fermentation using a bifido bacterium. Typically, one mole of glucose from the carbohydrate source is initially converted to about two moles lactate and the lactate is converted to about three moles acetate.

Acetic acid which is formed in connection with the fermentation can be in the form of acetate depending on the pH of the fermentation medium. The acetate can be acidified to form acetic acid. For example, the acetate can be reacted with carbonic acid in and an amine to form calcium carbonate and an amine complex of the acetate. The amine complex can be recovered and thermally decomposed to regenerate the amine and form acetic acid. The calcium carbonate can be recovered for reuse. The acetic acid can be esterified and hydrogenated to form an alcohol. Alternatively, the acetic acid may be directly hydrogenated to form ethanol. The esterification is preferably accomplished by reactive distillation.

In another embodiment of the present invention, the acetate can be acidified with carbon dioxide to produce acetic acid and calcium carbonate and esterified to acetate ester for recovery. Preferably, the process takes place at low or nearly atmospheric pressure. Preferably, the calcium carbonate is recycled to a fermentation broth in order to maintain a desired pH. Preferably, the ester is a volatile ester. As used herein, the term "volatile ester" means that the ester is capable of recovery by distillation, and therefore the ester should be more volatile than the water from which it is recovered. The alcohol employed in the esterification is preferably methanol, ethanol or mixtures thereof. The ester is preferably recovered by distillation, such as by reactive distillation, and subsequently converted to ethanol.

The reactive distillation can be accomplished by acidifying, esterifying and recovering the ester in a reaction column. A dilute solution of acetate salt in water mixed with ethanol is introduced near the top of a reaction section of the column. Carbon dioxide gas is introduced near the bottom of the reaction section of the column. The carbon dioxide reacts with acetate salt and ethanol in the reaction zone to form calcium carbonate and ethyl acetate. Ethyl acetate can be concentrated, e.g., by vaporizing a mixture containing excess ethanol in water and an azeotrope comprising ethyl acetate, water and ethanol. The azeotrope can be separated from the excess ethanol and water, e.g., by the addition of water, thereby causing a phase separation between an ethyl acetate-rich portion and a water and ethanol-rich portion. The ethanol and water can be returned to the reaction zone and the calcium carbonate can be recycled to a fermentation broth to control pH.

In one embodiment of the present invention, ethanol is produced from a carbohydrate source, with essentially none of the carbon and the carbohydrate source converting to carbon dioxide.

In another embodiment of the present invention, ethanol is produced from a carbohydrate source wherein at least 60%, preferably 70%, more preferably 80% and more preferably 90% and more preferably 95% of the carbon in the carbohydrate source is converted to ethanol.

In accordance with another embodiment of the present invention, an ester is recovered from a dilute solution of a carboxylic acid salt. The carboxylic acid salt is acidified with carbon dioxide to produce the corresponding carboxylic acid and calcium carbonate, and simultaneously esterified with an alcohol to form an ester. The ester is recovered. Preferably, the ester is a volatile ester and the alcohol is methanol, ethanol or mixtures thereof. The ester can be recovered by distillation, such as by reactive distillation. The ester can be converted to ethanol. The acidification, esterification and recovery can take place in a reaction column. Initially, a dilute solution of the carboxylic acid salt in water mixed with alcohol is introduced near the top of a reaction section of the column. Carbon dioxide gas is introduced near the bottom of the reaction section of the column. The carbon dioxide and carboxylic acid salt and alcohol react to form calcium carbonate and a volatile ester of the carboxylic acid salt. The ester can be concentrated by vaporizing a mixture containing excess alcohol and water and an azeotrope made up of the ester, water and alcohol. The azeotrope can be separated from the excess alcohol and water, e.g., by the addition of water, thereby causing a phase separation between an ester-rich portion and a water and alcohol-rich portion. The excess alcohol and water can be returned to the reaction zone.

In accordance with an embodiment of the present invention, a carbohydrate source and natural gas are converted to an easily transportable liquid product. The carbohydrate source is converted to acetic acid, acetate or mixtures thereof by fermentation. The acetic acid, acetate or mixtures thereof is converted to ethyl acetate. At least part of the ethyl acetate is converted to ethanol using hydrogen obtained from the natural gas source. The ethanol and/or ethyl acetate which is produced is then transported to a location remote from where it is produced. Preferably, the carbohydrate source and natural gas source are located within a distance that makes it economically feasible to produce the transportable liquid product, and the remote location is a sufficient distance away that it is not economically feasible to transport the carbohydrate and natural gas to the remote location for processing. Preferably, the economically feasible distance is less than about five hundred miles and the uneconomical remote distance is greater than about a thousand miles. For example, the natural gas source and carbohydrate source can be located on a Caribbean island such as Trinidad and the remote location can be on the Gulf Coast, such as the Texas Gulf Coast. Alternatively, the carbohydrate source and the natural gas source can be located in Australia and/or New Zealand and the remote location can be Asia, e.g., Japan, Taiwan, Korea or China.

In another embodiment of the present invention at least 80% of the carbon in a carbohydrate source is converted into ethanol. The method includes enzymatically hydrolyzing the carbohydrate source to sugars and amino acids. A carbohydrate, sugars and amino acids (from the original source or another source) are converted into lactic acid, lactate or mixtures thereof by homolactic fermentation. The lactic acid, lactate or mixtures thereof are converted into acetic acid, acetate or mixtures thereof by homoacetic fermentation. The pH of the fermentation broths are maintained in a range from about pH 6 to about pH 8, using a base. A biomass byproduct which is useful as an animal feed can be recovered from the fermentation. The acetate is acidified with carbon dioxide to produce acetic acid and calcium carbonate and the acetic acid is simultaneously esterified with an alcohol to form a volatile ester. The volatile ester can be recovered using reactive distillation. Hydrogen can be produced by any number of methods, e.g., steam reforming of natural gas. The acetate ester is hydrogenated to form ethanol.

DETAILED DESCRIPTION OF THE INVENTION

Figure 1:
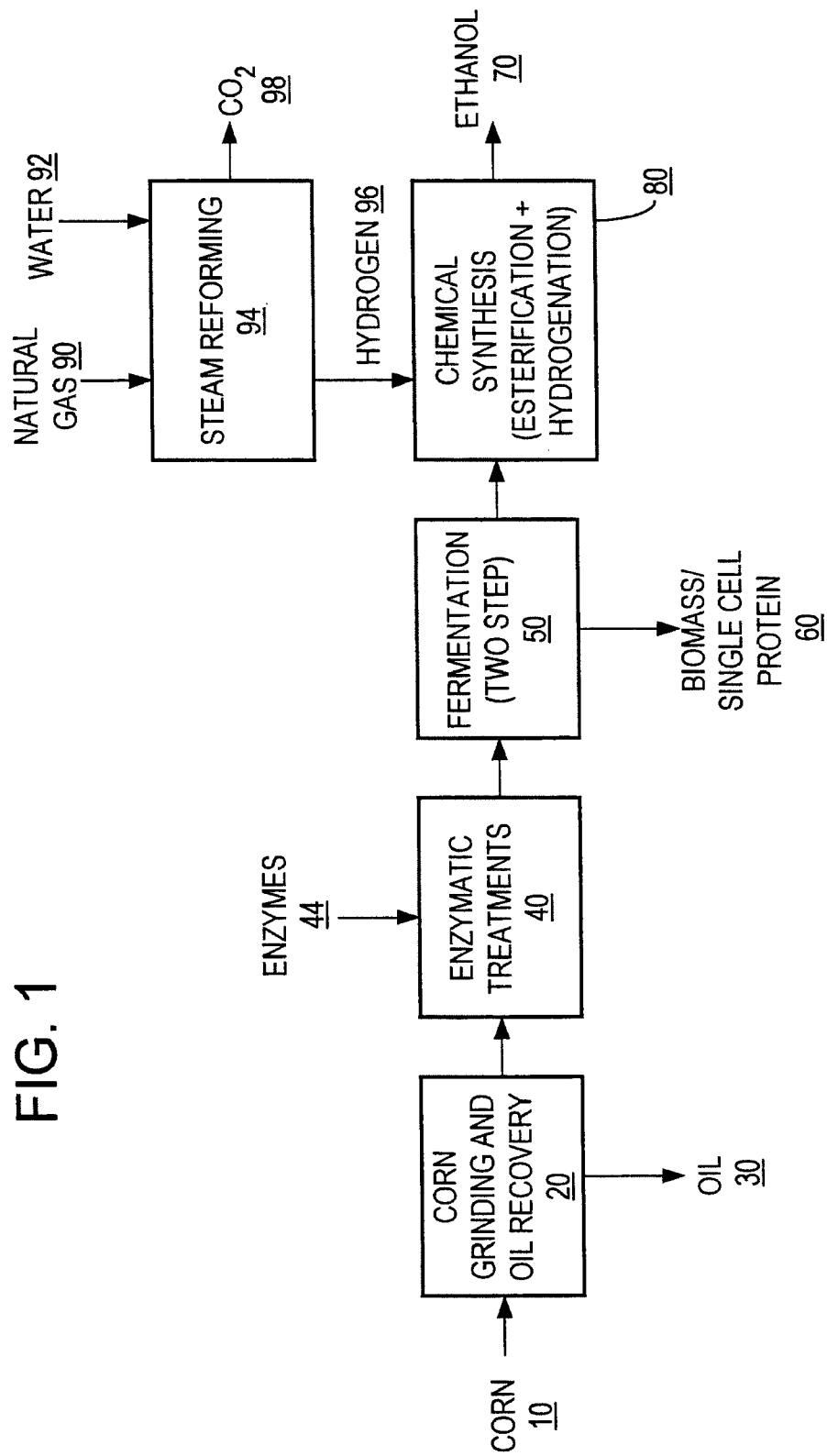
FIG. 1 is a block diagram of one embodiment of the process of the present invention.

One embodiment of the ethanol process of the present invention uses a unique combination of enzymatic milling, indirect fermentation, and chemical synthesis to produce a slate of high valued products. FIG. 1 is a simplified block flow diagram for the process. Corn 10 is ground 20 the oil 30 is extracted, and the remaining material is then enzymatically converted 40 using enzymes 44 into fermentable sugars and amino acids. Acetic acid and bacterial biomass 60 are produced by a two step fermentation 50. The first step uses a lactic acid bacteria such as *Lactobacillus casei* to convert the fermentable sugars into lactic acid. The second fermentation step uses an anaerobic bacteria such as *Clostridium formicoaceticum* to convert the lactic acid and residual sugars from the first fermentation into acetic acid without any $CO_2$ byproduct. This combination of fermentation steps results in a high yield of acetic acid with the coproduction of bacterial biomass 60 that can meet the US FDA requirements on direct-fed microbials. The resulting acetic acid is converted into ethanol 70 using chemical synthesis steps (esterification+ hydrogenation) 80. The bacterial biomass 60 from the fermentations is directly usable or can be processed into a high protein animal feed concentrate called Single Cell Protein (SCP) 60.

The overall chemistry for the major steps are as follows:

| Enzymatic Treatment: | (1/n) Starch + $H_2O$ | -> Dextrose |
|---|---|---|
| Fermentation 1: | Dextrose | -> 2 Lactic Acid |
| Fermentation 2: | 2 Lactic Acid | -> 3 Acetic Acid |
| Esterification: | 3 Acetic Acid + 3 Ethanol | -> 3 Ethyl Acetate + 3 $H_2O$ |
| Steam Reforming: | 1.5 Methane + 3 $H_2O$ | -> 1.5 $CO_2$ + 6 $H_2$ |
| Hydrogenation: | 3 Ethyl Acetate + 6 $H_2$ | -> 6 Ethanol |
| Overall: | (1/n) Starch + 1.5 Methane + $H_2O$ | -> 3 Ethanol + 1.5 $CO_2$ | where n is the number of dextrose units in a starch molecule. The above equations show starch as the only source of fermentable sugars in corn. However, the ethanol process of the present invention uses an enzymatic milling process which also makes the cellulose and hemicellulose fractions of corn available for fermentation. The enzymatic milling process increases the amount of fermentable sugars derived from a given amount of corn by about 20% over traditional wet milling.

Another reason for the high yield of the ethanol process of the present invention is the amount and source of the $CO_2$ produced by the present process. In the ethanol process of the present invention, only 0.5 moles of $CO_2$ are produced for every mole of ethanol. In contrast, traditional fermentation routes produce 1 mole of $CO_2$ for every mole of ethanol. Furthermore, the ethanol process of the present invention uses less expensive methane rather than dextrose as the carbon source for carbon dioxide. Lower $CO_2$ production from less expensive feedstocks leads to better process economics.

Preparation of Suitable Fermentation Substrate

There are many processes which are well known in the state of the art to provide suitable fermentation media for lactic acid or acetic acid fermentations. These can be media which minimize the amount of nitrogen in the media and thus minimize the amount of single cell protein. On the other hand there are processes which attempt to increase the utilization of nitrogen in the feed.

Any suitable media preparation process may be used for the purposes of this invention.

As an illustrative example only, one can consider using corn as the raw material. Several pretreatment steps are typically used in corn milling such as cleaning, germ removal for oil production, etc as is well know to those in the milling art.

Typically enzymatic treatment is used to convert the corn into a media that is suitable for metabolism by the bacteria in the downstream fermentations, although acid hydrolysis has also been used. The ground corn is mixed with water to form a slurry which is then heat sterilized. A continuous sterilizer that heats the corn slurry to 120-140 C and provides 1 to 5 minutes of residence time can be used. Preferably, the retention tubes are designed to provide turbulent flow (Re>4000) with minimal dead spots, so that good sterilization without excessive carmelization occurs.

Heat sterilization also begins the liquefaction process. During liquefaction the starch granules swell and the viscosity of the slurry rises dramatically. Heat stable a-amylase is used to limit the rise in viscosity by depolymerizing the starch molecules—a process called saccharification. a-amylase is an enzyme which hydrolyzes the 1,4 linkages in the starch molecule. It is classified as an endoenzyme since it randomly attacks bonds in the interior of the starch molecule. Sufficient reduction in viscosity is achieved with 10-15% hydrolysis of the starch in less than 10 minutes residence time at pH 5.5-7.0.

Glucoamylase is preferably used to complete the hydrolysis of the starch molecule. Glucoamylase is an exoenzyme since it only attacks the ends of the starch molecule. The enzyme hydrolyzes both 1,4 and 1,6 linkages, so nearly complete hydrolysis of the starch can be achieved. Optimal conditions for glucoamylase are typically 58-62 C, pH 4.4-5.0, and 24-48 hours of residence time. Longer residence times are typically not beneficial since the enzyme also catalyzes the formation of non-fermentable disaccharides—processes called reversion and retrogradation.

In addition to the utilization of the starch fraction of corn it is desirable to utilize the other major fractions, including the hemicellulose and cellulose, as well as the protein in this invention. This is not typically done in current ethanol processes. The higher yield of this invention and the wide substrate utilization capability of the fermentation used enhance the value of these added steps as opposed to the current processes as will be shown.

Hydrolysis of hemicellulose can be carried out in several ways. Much research is known on acid hydrolysis, but enzymatic hydrolysis is also well known. Complete enzymatic hydrolysis of hemicellulose requires a mixture of enzymes. The pendant arabinose and glucuronic acids are removed from the xylose backbone using a-L-arabinofuranosidase and a-glucuronidase. The xylose backbone is hydrolyzed using endo-b-1,4-xylanase and b-xylosidase.

Cellulose utilization is also of value. Several methods are know for the hydrolysis of cellulose to fermentable sugars. For example, cellulose is hydrolyzed by the synergistic action of three cellulase enzymes: endo-b-glucanase, exo-b-glucanase, and b-glucosidase. The endo-b-glucanase is an endoenzyme which randomly hydrolyzes the 1,4 linkages in the interior of the cellulose molecule. Exo-b-glucanase removes cellobiose units (a disaccharide of b linked glucose) from the non-reducing end of the cellulose chain. b-glucosidase hydrolyzes a cellobiose unit into two glucose molecules. Working together, the three enzymes can convert cellulose into glucose monomer. It is also a feature of this invention that lactic acid bacteria as used in this invention utilize cellobiose directly which reduces feedback inhibition of the hydrolysis.

The hemicellulose and cellulose enzymes have been the focus of much research work over the past 10-20 years. These enzymes are required for efficient conversion of woody biomass materials into fermentable sugars, which can then be used as fermentation feedstocks for ethanol and other fermentation products by traditional processes. Biomass materials such as grass, wood, paper, and crop residues are much less expensive than starch based materials such as corn starch.

Redaction in enzyme cost can be obtained by overlapping the saccharification activity with the fermentation process in a design called Simultaneous Saccharification and Fermentation (SSF). Product inhibition of the cellulases is avoided by conversion of the glucose into ethanol or other desired fermentation product. The SSF philosophy has been used for decades by the ethanol industry with starch enzymes. Research also shows that this concept works for the hemicellulase and cellulase enzyme systems. This process may also be used in the current invention. It is a preferred process because the fermentation used in this invention utilizes more of the types of sugars produced in the hydrolysis and further accelerates the hydrolysis compared to a yeast fermentation which consumes the glucose fraction largely.

In addition to the utilization of the fiber fraction comprising hemicellulose and cellulose, it may be desirable in this invention to utilize the protein fraction.

Protease enzymes are used to hydrolyze the corn proteins into smaller peptides and amino acids. These amino acids and peptides are a major nitrogen source for the fermentation bacteria. Hydrolysis of the proteins is required to speed nitrogen assimilation in the fermentation. U.S. Pat. No. 4,771,001 shows the use of protease enzymes to increase the utilization of proteins by a lactic acid fermentation. This patent also illustrates the use of a different raw material, in this case cheese whey. For the purposes of the current invention the protein used to supplement the fermentation can come from the corn as illustrated, or from other protein sources and can be mixed into the media. Any protein source that produces a suitable fermentation media for lactic acid or acetic acid fermentation and does not inhibit the fermentation may be used.

In its most general embodiment the current invention does not depend upon a specific carbohydrate or protein source, but any suitable source may be used.

Fermentation

The overall purpose of the fermentation part of the current invention is to convert the fermentable carbohydrates and amino acids into acetic acid and single cell bacterial protein. In a preferred embodiment a two step fermentation process is used. The first step uses a homofermentative lactic acid bacteria to convert the bulk of the fermentable sugars into lactic acid and single cell protein. The second step uses a homofermentative acetogenic bacteria to convert lactic acid and residual carbohydrates into acetic acid.

The tactic acid fermentation step uses a homofermentative lactic acid bacteria such as *Lactobacillus casei* to convert the fermentable sugars into lactic acid. Lactic acid bacteria are gram-positive, non-spore forming, aerotolerant anaerobes. These bacterial are found in the mouths and intestinal tracts of most warm blooded animals including for use in direct-fed microbials for animal feeds. Viable cultures are also present in many yogurts consumed by humans.

Figure 2:
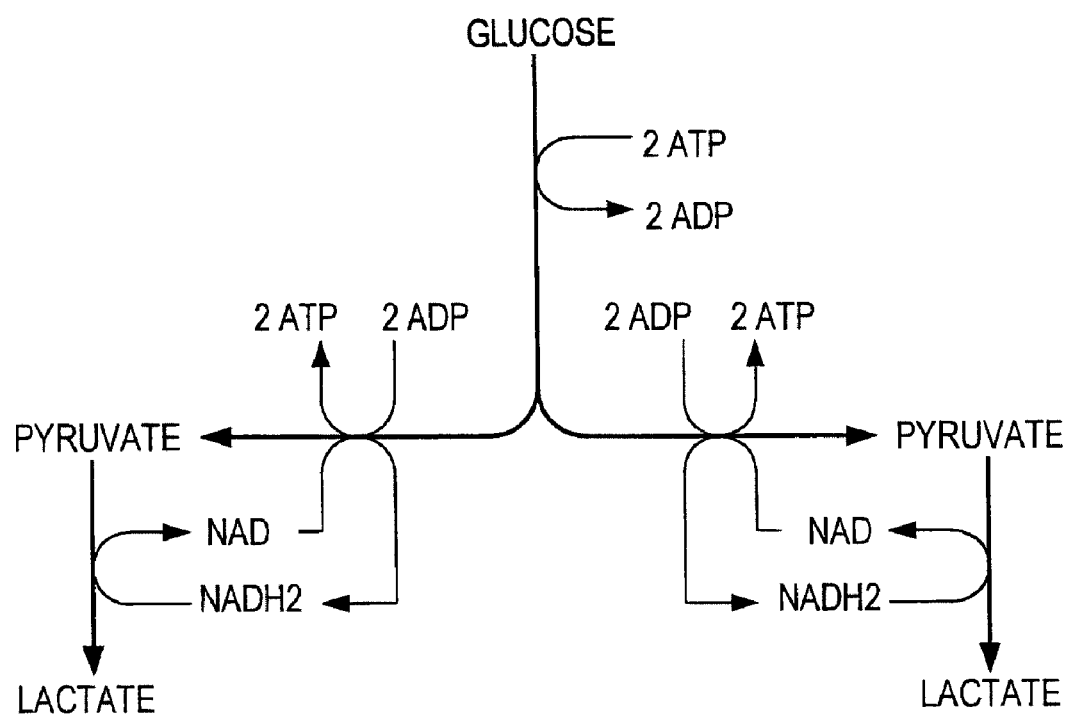
FIG. 2 illustrates the metabolic pathway for the conversion of glucose to lactate.

As shown in FIG. 2, lactic acid is the sole metabolic product for homofermentative strains. Glucose is metabolized to pyruvate using the regular Embden-Meyerhof glycolytic pathway. Pyruvate is convert to lactic acid in a single NAD coupled step. Most lactic acid bacteria are mesophilic with optimal temperatures for growth between 35 to 45 C. Cell growth is pH sensitive with optimal pH around 6.0. Product inhibition begins to affect the kinetics of cell growth and acid production at lactic acid levels above 4 wt %. Complete inhibition of growth occurs around 7 wt % while complete inhibition of acid production occurs around 10-12 wt %.

The feed to the fermentation is very dilute in carbohydrates with only about 5 wt % fermentable sugars. A single stage continuous stirred tank reactor (CSTR) type fermentor is appropriate for this step. However, any suitable bioreactor can be used, including batch, fed-batch, cell recycle and multi-step CSTR. The low carbohydrate concentration in the feed will limit the effects of product inhibition on the cell growth and acid production kinetics, thus 90+% conversion of the dextrose with about 18-24 hour residence times is possible. Most homofermentative strains will readily metabolize a range of substrate sugars. It is advantageous to combine the lactic acid fermentation with the subsequent acetic acid fermentation in such a manner so as to utilize all of the sugars.

In contrast to many industrial lactic acid fermentations, the current invention may be operated in a mode in which the fermentation is carbohydrate limited rather than nitrogen limited. Thus biomass production is maximized by keeping most of the fermentation in the growth associated state and ensuring that sufficient nitrogen is available for growth. For any growth associated fermentation the biomass yields are typically about 10.5 g per mole of ATP produced. Since lactic acid fermentations produce a net of 2 moles of ATP per mole of glucose, the biomass yield will be around 2 (10.5/180)=0.12 g per g of glucose. By stoichiometry, the remaining 0.88 g of glucose are converted into 0.88 grams of lactic acid.

The efficient production of biomass as single cell protein is an important part of this invention. In contrast to the production of single cell protein historically, the use of an anaerobic homofermentative fermentation is very advantageous. This is because all of the energy production of the organism comes from the production of the desired metabolite whether lactic acid or acetic acid. This means that there is no wasted byproduct $CO_2$ as is the case in aerobic fermentations. In addition, because of the lack of production of $CO_2$, the heat produced by the fermentation is also minimized. Therefore the utilization of energy contained in the raw material carbohydrates is maximized toward the production of valuable single cell protein or lactic and acetic acid. The traditional yeast fermentation, in addition to wasting mass as $CO_2$, also requires the removal of heat.

The fermented broth from the first fermentation step is clarified using a centrifuge. The concentrate contains the lactic acid bacteria and is sent to single cell protein recovery. The amount of single cell protein produced is related to the amount of nitrogen in the form of hydrolyzed proteins as amino acid and peptides that is supplied to the fermentation in the medium. This can range from a very small amount, but not zero, as lactic acid bacteria require some complex nitrogen sources, such as 1% up to about 15% overall yield of single cell protein based on the total nitrogen plus carbohydrate in the medium. It is a feature of the invention that the production of single cell protein can be controlled over a wide range. The single cell protein can be processed by any suitable means, such as spray drying, to produce a salable product.

Another important feature of the current invention is the production of a single cell protein which is enhanced in value as an animal feed ingredient. The single cell protein from the lactic acid fermentation has these features. It has a high protein concentration of about 70%, depending on the strain of organism and the specific conditions of the fermentation. It has a good amino acid profile. That is, it contains a high percentage of so called essential amino acids comprising, for example, lysine, methionine, isoleucine, tryptophan, and threonine. The combined percentage of these amino acids in lactic acid bacteria is about 10.5%, compared to corn protein which has about 1% of the total corn kernel. The protein composition of corn depends on the fraction of the corn considered. Corn gluten meal, for example, has about 7.5%, but corn gluten feed has about 2.5% of essential amino acids. This enhanced amino acid composition is directly related to the value of the protein as an animal feed ingredient.

In a preferred embodiment, the current invention can produce single cell protein at high efficiency and with high value.

The centrate, from the separation of the lactic acid bacteria from the fermentation broth of the first fermentation, is fed to a second fermentor where the lactate is converted into acetate using an acetogenic bacteria. Lactate can be a preferred substrate for acetogenic bacteria in many of their natural environments. The rate of fermentation and yield on lactate substrate can be very high, e.g., over 98% yield of acetate from lactate.

Incomplete removal of the lactic acid bacteria is typically acceptable since the acetic acid fermentation typically uses a thermophilic strain and the second fermentation is done at a higher temperature. Contamination of the acetic acid fermentation with a mesophilic lactic acid bacteria is typically not an issue since the lactic acid bacteria typically cannot grow at these higher temperatures. Also, near complete conversion of the glucose is expected in the first fermentor, so the lactic acid bacteria which do happen to bleed through the centrifuge into the second fermentor will not have a carbohydrate source.

The acetogenic bacteria have been known and studied since the 1930's. Drake, H. L. (editor), *Acetogenesis*, Chapman & Hall, 1994, gives a good overview of the field. The acetogenic bacteria include members in the *Clostridium, Acetobacterium, Peptostreptococcus* and other lesser known species. The habitats of these bacteria are: sewers, anaerobic digesters at municipal waste treatment plants, natural sediments, termite guts, rumens, and intestinal tracts of non-ruminants including humans. Pathogenicity is rare. All of these organism are strict anaerobes, which means that contact with oxygen is often fatal to the microorganism. *Clostridium* are spore formers. Spores are resistant to many sterilization techniques and special procedures have been established for handling spore-forming bacteria. The *Acetobacterium* and *Peptostreptococcus* species are not spore formers.

Figure 3:
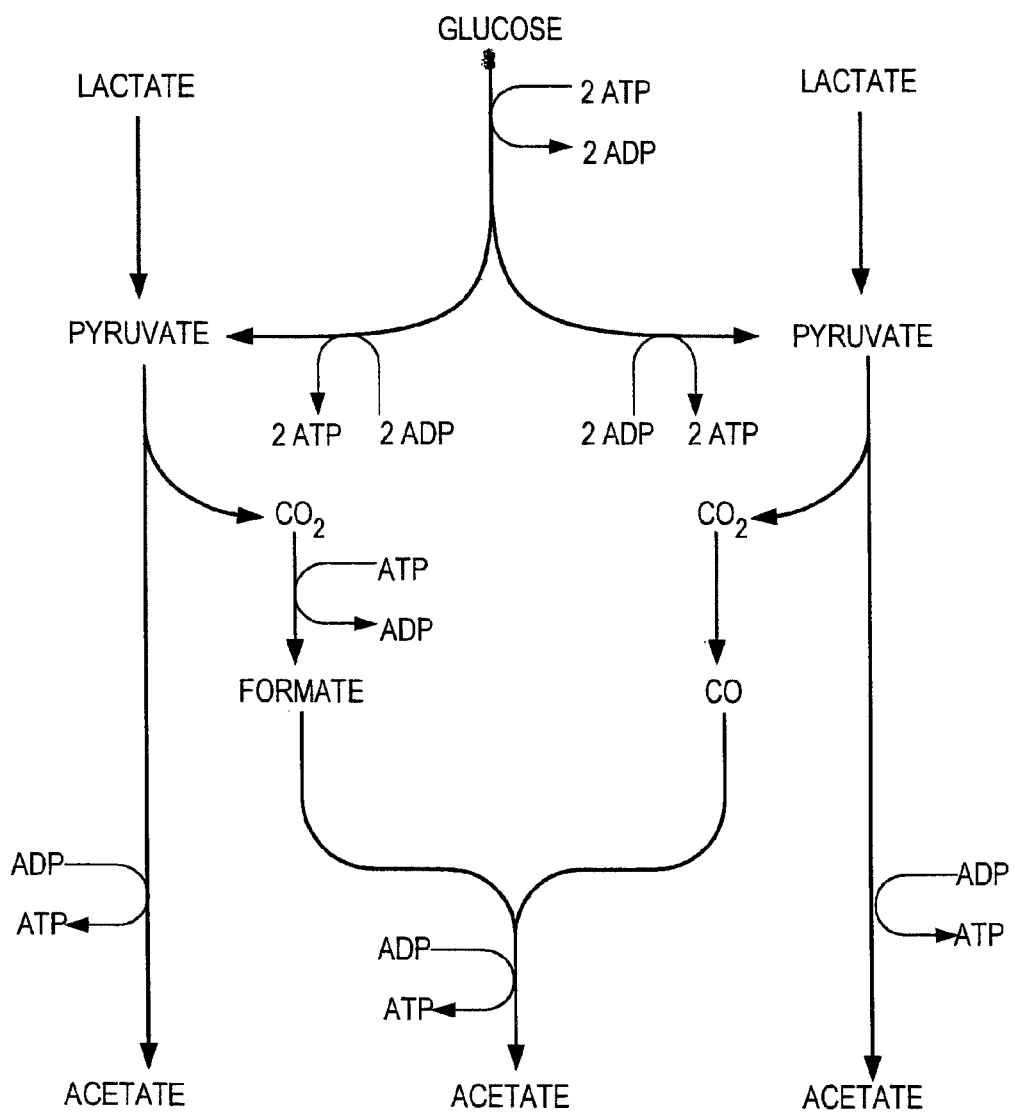
FIG. 3 illustrates the metabolic pathway for the conversion of glucose to acetate.

FIG. 3 is a simplified sketch of the metabolic pathways used by most acetogenic bacteria. The organism metabolizes glucose to pyruvate using the normal Embden-Meyerhof glycolytic path. Lactic acid is also metabolized by first converting it back to pyruvate. From pyruvate, the organism makes acetic acid and carbon dioxide using the regular oxidation pathways. The main distinguishing feature of acetogenic bacteria is that acetogenic bacteria have a metabolic pathway which will fix the $CO_2$ and make an additional mole of acetic acid.

The novel acetogenic pathway provides three functions for the organism:

1. Like all anaerobes, a terminal electron acceptor other than oxygen is required to balance the redox reactions of metabolism. In this case, the reduction of carbon dioxide acts as the electron sink.
2. Cellular energy (i.e. ATP) is produced from this pathway. The metabolic pathways for conversion of one mole of glucose into two moles of acetic acid and two moles of carbon dioxide produce four ATP per mole of glucose consumed. Addition of the acetogenic pathways creates another acetic acid molecule from the carbon dioxide and increases the ATP yield to 4-6 ATP per mole of glucose. The additional ATP are not made directly from the substrate-level phosphorylation but are made in other processes such as the electron transport chain and from ion pumps located in the cell membranes. The exact amount of ATP produced from the secondary sources varies from strain to strain and is also dependent upon the cell environment.
3. Carbon dioxide can be converted into cellular carbon needed for growth using the cell's anabolic pathways, even when common carbon sources such as glucose are not available.

Some acetogens will produce other organic acids such as formic, propionic, succinic, etc. in addition to acetic acid. These organisms are described as heterofermentative as opposed to the homofermentative organisms which only produce acetic acid. The heterofermentative pathways represent a potential yield loss in the current invention, and proper strain selection and elucidation of the factors which cause the formation of these other organic acids will minimize the impact.

By far, most work to date has been with the *Clostridium* strains. Many of these strains are thermophilic with optimal temperatures for growth around 60 C. Several kinetic studies (Yang, S. T., Tang, I. C., Okos, M. R., "Kinetics and Mathematical Modeling of Homoacetic Fermentation of Lactate By *Clostridium formicoaceticum*", Biotechnology and Bioengineering, vol. 32, p. 797-802, 1988, Wang, D. I., Fleishchaker, R. J.; Wang, G. Y., "A Novel Route to the Production of Acetic Acid By Fermentation", AIChE Symposium Series-Biochemical Engineering: Renewable Sources, No. 181, vol. 74, p. 105-110, 1978; and Tang, I. C., Yang, S. T., Okos, M. R., "Acetic Acid Production from Whey Lactose by the Co-culture of *Streptococcus lactis* and *Clostridium formicoaceticum*", Applied Microbiology and Biotechnology, vol. 28, p. 138-143, 1988, which are incorporated herein by reference in their entirety) have been conducted to examine the effects of pH and acetate levels on both cell growth and acid production. These organism are sensitive to low pH and product inhibition occurs at much lower concentrations than in lactic acid bacteria. Optimal pH is around 7 and maximum acetate tolerance is only about 30 g/l in batch fermentation.

A one or two stage CSTR fermentor design is typically appropriate for the second fermentation step. However, any suitable bioreactor can be used, including batch, fed-batch, cell recycle, and multi-step CSTR. In contrast to the first fermentation step, the acetic acid fermentation is nitrogen limited rather than carbohydrate limited. Yield of acetic acid from lactic acid can be greater than 85% of theoretical.

In one embodiment, the broth from the second fermentation step is prepared for the second part of the current invention which is the chemical conversion. As an example, the broth is clarified with a combination of a centrifuge and a microfilter. The centrifuge removes the bulk of the biomass and reduces the size of the downstream microfilter by reducing its load. The microfilter permeate is sent to a nanofiltration unit. The microfilter acts as a prefilter for the nanofiltration unit. The nanofiltration unit removes proteins, unconverted sugars, etc. which have molecular weights above about 300. The nanofiltration unit removes the bulk of the impurities in the acetate broth and produces a water white permeate that can be sent to downstream processes.

The concentrates from the centrifuge, microfilter and nanofilter may be processed to recover values useful in the single cell protein or recycled to one of the fermentation steps. Alternatively, they may be disposed of in any acceptable manner such as composting or incineration.

Although a preferred embodiment of the current invention utilizes two fermentation steps and the production of single cell protein, this is not required in the most general case. A suitable medium for the acetic acid fermentation alone may be provided. Although single cell protein may not be produced, the increased yield form the carbohydrate source will still provide an important advantage for the current invention.

In addition, it is not necessary to utilize the hemicellulose or cellulose fraction of the raw material in order to get the advantages of the current invention. An example is the utilization of the invention in conjunction with a corn wet mill where the medium would be almost pure starch and corn steep water produced by the mill. The current invention would still increase the ethanol yield compared to current technology by 75% providing a huge economic advantage.

The key feature of the fermentation step is therefore the conversion of carbohydrate from any source into acetic acid.

Acidification and Esterification

In the next step of the invention, the acetic acid or acetate produced in the fermentation is converted to an ester of acetic acid, preferably methyl or ethyl ester and more preferably ethyl ester. Any suitable process that will convert the acetic acid or acetate salt to the ester is acceptable as part of this invention.

Acetic acid is a weak organic acid with pKa=4.76. If the fermentation is conducted at near neutral pH (i.e. pH=7.0), the product of the fermentation will actually largely be an acetate salt rather than the acid. In the fermentation, any suitable base can be used to neutralize the fermentation. The preferred neutralizing agent is $Ca(OH)_2$, which can be supplied by CaO (lime) or calcium carbonate ($CaCO_3$) which can be recycled from later in the process. Other neutralizing agents can be used, such as NaOH or $NH_2OH$, as determined by the conditions required by the fermentation organism. However, even the acetate salt is inhibitory and the maximum concentration of acetate is usually limited to about 5% in the fermentation broth.

Thus, there are two problems in the recovery of acetic acid salts from a solution such as a fermentation broth. The acetate salt must usually be converted to the acid, and the acid must be removed from the dilute solution in water. In addition it is desirable to recycle the base used to neutralize the fermentation to reduce costs and avoid potential environmental impact.

The most typical route is the sequential acidification of the salt to produce acetic acid and then the subsequent recovery of the acid. Even after the salt is converted to a dilute acid solution, there is still the need to recover the product from the water. Many different process approaches have been proposed to recover such dilute solutions. Since acetic acid has a higher boiling point than water, the bulk of the water, about 95% of the broth, must be distilled away from the acetic acid to recover the acid if simple distillation is used. Alternatively, some more complex process may be used to recover the acetic acid, usually in conjunction with solvent extraction. However this line of research, that is, acidification with subsequent recovery from the dilute solution, has not overcome the economic limitations of the acetic acid fermentation process to make it competitive with the synthesis gas based route. Therefore, all industrial acetic acid is currently made from synthesis gas derived from coal, petroleum or natural gas.

A number of methods have been proposed to acidify the acetic acid salt solution. One method is the reaction of the acetate salt with a strong acid such as sulfuric acid to form acetic acid (HAc) and calcium sulfate ($CaSO_4$). The $CaSO_4$ precipitates and is easily separated from the acetic acid solution. However, this method requires the consumption of acid and base and produces a byproduct waste salt that may become an environmental burden. Another method is bipolar electrodialysis that splits the salt into an acid and base (this does not work well with Ca salts, but one could substitute Na in this case). Other routes to produce dilute acetic acid from the salt are well known.

Reaction of a carboxylic acid salt with an amine and $CO_2$ with the precipitation of $CaCO_3$ and the formation of an acid amine complex that can be extracted and thermally regenerated has also been proposed, as shown by U.S. Pat. No. 4,405,717, which is incorporated herein by reference in its entirety.

U.S. Pat. No. 4,282,323, which is incorporated herein by reference in its entirety, discloses a process to acidify acetate salts using $CO_2$ in a number of ways. In the referenced patent the acetic acid formed is removed by a solvent to a separate phase.

Esterification of acetic acid to form ethyl acetate is a well understood reaction:

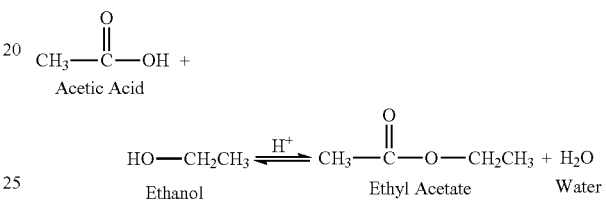

Esterification is typically performed in the liquid phase. The equilibrium constant for this reaction is 4.0 and is nearly independent of temperature. Acid catalysts for the reaction include: strong Bronsted acids such as sulfuric acid and methane sulfonic acid, acidic ion exchange resins, zeolites, and a number of other materials, including carbonic acid formed by the dissolution of $CO_2$ in water. The reaction rate is influenced by the type and concentration of catalyst, the reaction temperature, and the degree of departure from equilibrium.

Alternative routes exist that attempt to avoid the separate acidification and esterification steps. A carboxylic acid salt may be reacted directly with an alcohol such as ethanol to produce the ester directly. An intermediate step may be inserted to convert the Ca salt to an ammonia salt. In this step the dilute $Ca(Ac)_2$ is reacted with $NH_3$ and $CO_2$ to form $NH_4Ac$ and $CaCO_3$ which precipitates. The ammonia salt of acetic acid may then be esterified directly as shown by U.S. Pat. No. 2,565,487, which is incorporated herein by reference in its entirety.

Preferred Approach

The preferred approach is to combine chemical and phase change operations into a new efficient process to directly produce a volatile ester of acetic acid and distill the ester away from the broth.

The three parts are:

1) Acidification of the fermentation broth with $CO_2$ at low or nearly atmospheric pressure to produce acetic acid and precipitate $CaCO_3$ which can be recycled directly to the fermentation as the base;

2) Simultaneous esterification of the formed acetic acid with an alcohol, such as methyl or ethyl alcohol, to form a volatile ester, and 3) Reactive distillation to push the acidification and esterification equilibria to high conversion.

Since esterification is an equilibrium reaction, high conversion can be obtained by driving the reaction to the right with continuous removal of one or more products. Reactive distillation similar to that developed by Chronopol for lactide synthesis (See U.S. Pat. No. 5,750,732, which is incorporated herein by reference in its entirety) and by Eastman Chemical for methyl-acetate production (see U.S. Pat. Nos. 4,939,294 and 4,435,595 and Agreda, V. H., Partin, L. R., Heise, W. H., "High-Purity Methyl Acetate Via Reactive Distillation", Chemical Engineering Progress, p. 40-46, February 1990, which are incorporated herein by reference in their entirety) is an economically attractive method. U.S. Pat. No. 5,599,976, which is incorporated herein by reference in its entirety, discloses the conversion of very dilute acetic acid to the ester in a continuous reactive distillation process. Xu and Chaung (Xu, Z. P, Chuang, K. T., "Kinetics of Acetic Acid Esterification over Ion Exchange Catalysts", Can. J. Chem. Eng., pp. 493-500, Vol. 74, 1996) show that reactive distillation to produce the ester of acetic acid from dilute solution is the preferred method to remove acetic acid from very dilute solutions, as are produced in the current invention. In this concept, the acetic acid flows in a counter current fashion to the esterifying ethanol in a distillation column. In the current invention, ethyl acetate is more volatile than acetic acid so the ethyl acetate is distilled away from the liquid mixture and the esterification reaction is pushed to the right, thus enabling high conversions in a single vessel. The process proposed here goes beyond these examples in that its combines simultaneous acidification with the reactive distillation esterification. All of the cited processes start with acetic acid (or lactic acid in the Chronopol case) and not a salt.

The net effect of the reactive distillation process, the preferred route, is to remove the acetic acid from the dilute solution without vaporizing the water which forms the bulk of the stream.

Figure 4:
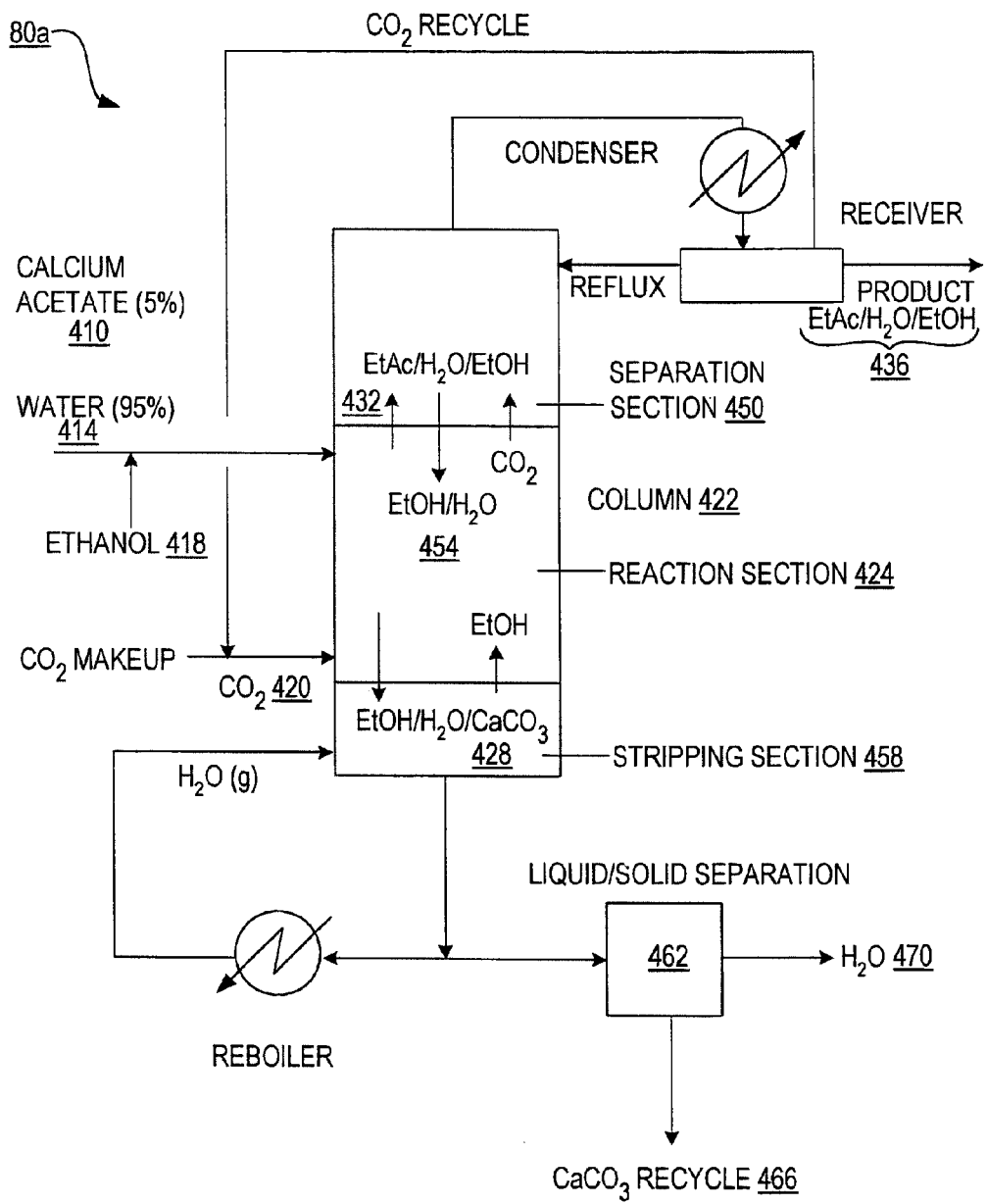
FIG. 4 illustrates one embodiment of reactive distillation.

In addition, the use of $CO_2$ as the preferred acidifying agent with the precipitation of $CaCO_3$ allows the recycle of the neutralizing agent to the fermentation without the consumption of chemicals. The $CaCO_3$ can be used directly in the fermentation or can be converted first to CaO by calcination. The reactive distillation process 80a is shown in FIG. 4.

Reaction section: The raw material, a dilute (5%) solution of calcium acetate 410 ($Ca(Ac)_2$) in water 414 is mixed with ethanol 418 and fed to the column 422 at the top of the reaction section 424. $CO_2$ 420 is fed to the column 422 at the bottom of the reaction section 424. The simultaneous reaction of $CO_2$ 420 with $Ca(Ac)_2$ 410 and ethanol 418 takes place in the reaction zone 424 in the center section of the column 422 with the formation of $CaCO_3$ 428 and ethyl acetate (EtAc) 432.

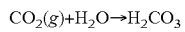

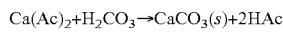

The most volatile component in the reaction mixture is the ethyl acetate/water/ethanol azeotrope 436. The azeotrope composition is 82.6% ethyl acetate, 9% water and 8.4% ethanol and has a normal boiling point of 70.2° C. The azeotrope 436 is removed from the reaction mixture by vaporization along with some EtOH and water. The bottom product from the reaction zone is a water and ethanol solution containing the suspended $CaCO_3$ flowing to the stripping section.

Separation Section: In the upper separation zone 450 the azeotrope is separated from the ethanol and water also vaporized from the reaction mixture. The ethanol water mixture 454 is recycled to the reaction zone 424 and the overhead product is the azeotrope 436. The $CO_2$ is separated from the overhead condensate and recycled to the column with makeup $CO_2$. The azeotrope can be broken by the addition of water, which causes a phase separation, with the water and ethanol rich phase returned to the appropriate point in the reactive distillation column (not shown).

Stripping Section: Since excess ethanol is used to favor the forward esterification reaction in the reaction section, the stripping section 458 returns the excess ethanol to the reaction zone. In the stripping section 458 the ethanol is removed from the $CaCO_3$-containing water stream which is discharged from the column 422 and separated by a simple liquid/solid separation 462 such as centrifugation or filtration, into the solid base 466 for recycle and water 470.

The net effect of the reactive distillation process is to recover the acetic, acid from the dilute salt solution thereby producing a relatively concentrated product stream at the top and without vaporizing the water that forms the bulk of the stream. The integration of the three sections reduces the energy requirement. The simultaneous removal of the product ester shifts the esterification equilibrium and leads to higher conversion in a short time.

It is unusual to handle precipitates in a distillation system. However, in this case the precipitation reaction occurs in the bulk phase and is not due to the concentration of the solution at a heat transfer surface, a common type of fouling. Ethanol beer stills in the corn dry milling ethanol industry typically handle solids loading in the stripping section through the use of trays with simple construction and large openings. Alternatively, it would be possible to operate the reaction section in other configurations, such as a series of stirred tanks with a common vapor manifold, to simulate the column reaction section.

The successful development of a low cost, low energy, integrated acidification, esterification and purification process for ethyl acetate would potentially allow the economic production on an industrial scale of major chemicals from renewable resources, which are now produced from non-renewable resources.

One major benefit of using renewable resources is the reduction of $CO_2$ production with the replacement of fossil raw materials. There would be a benefit to the U.S. economy from the replacement of imported petroleum with domestic renewable resources. The use of agricultural commodities to produce chemicals and liquid fuels without subsidy has important benefits to the farm community in terms of product demand and stable markets and reduces the cost of U.S. government subsidies.

Hydrogenation

The third major step in the invention is the conversion of the ester of acetic acid into two alcohols by hydrogenation. The hydrogenation of esters to produce alcohols is a well-known reaction.

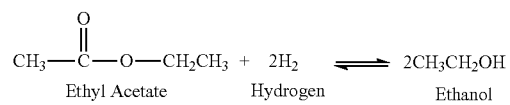

U.S. Pat. Nos. 2,782,243, 4,113,662, 4,454,358, and 4,497,967, which are incorporated herein by reference in their entirety, disclose processes for the hydrogenation of esters of acetic acid to ethanol.

For the particular case at hand, hydrogenation can be performed in either the liquid phase or the gas phase. Any suitable hydrogenation process can be used. This reaction is also an equilibrium reaction. The reaction can be driven to the right by using high partial pressures of hydrogen. Typical reaction conditions are 150-250 C and 500-3000 psi depending upon the desired conversion and selectivity. The reaction can be catalyzed by any suitable hydrogenation catalysts, such as copper chromite, nickel, Raney nickel, ruthenium, and platinum. A copper chromite, nickel, or Raney nickel catalyst is preferred for the hydrogenation since these catalysts are not poisoned by water. In the liquid phase process, an alcohol such as ethanol is a good solvent.

In the gas phase process, the ethyl acetate feed is vaporized and fed to the hydrogenation reactor with an excess of hydrogen. After passing through the bed, the vapors are cooled and flashed into a low pressure knockout drum. The hydrogen rich vapor phase is recycled back to the reactor. The liquid phase is distilled to remove residual water and unreacted ethyl acetate. The water is not made by the hydrogenation chemistry; it's source is the liquid-liquid equilibrium level present in the upstream reflux drum of the reactive distillation column.

Another distillation column may be needed as a final polishing step, depending upon the nature and quantities of side products from the esterification and hydrogenation units.

The preferred ester is ethyl acetate, as it avoids the introduction of a second compound into the process which must be purified away from the product stream.

The water stripper collects water streams from the acidification, esterification, and hydrogenation units. The water is steam stripped to recover solvent values, then the water is sent to final treatment and discharge or recycled to the fermentation section.

Many potential sources of hydrogen for use in the present invention exist. Any suitable hydrogen source can be used that produces hydrogen of sufficient purity for the hydrogenation reaction and that will not poison the catalyst. Raw materials for hydrogen production include water from which hydrogen can be produced by electrolysis. Many fossil and renewable organic feedstocks can also be used. If a fossil feedstock is used, such as methane from natural gas, some $CO_2$ will be produced along with the hydrogen. However, if a renewable feedstock is used then the $CO_2$ production will be neutral to the environment. For example, feedstocks which contain carbon and hydrogen at the molecular level can be used to produce hydrogen. Wood chips, sawdust, municipal wastes, recycled paper, wastes from the pulp and paper industry, solid agricultural wastes from animal and/or crop production are all examples of renewable feedstocks that can be used for hydrogen production, e.g., using gasification technology.

Steam reforming of methane to produce hydrogen is a well know process. As shown in FIG. 1, natural gas 90 and water 92 are reacted in a steam reformer 94 to form hydrogen 96 and carbon dioxide 98. Other methods to produce hydrogen (partial oxidation of hydrocarbons, partial oxidation of coal, water electrolysis, etc.) could also be used. Where pure oxygen is available, such as in a fenceline operation with an air separations plant, the partial oxidation processes can be economically viable. Where inexpensive sources of electricity are available, electrolysis can be viable.

Another advantage of the current invention, compared to prior art technology for ethanol production, is the heat balance in the process. In the current invention, if hydrogen is made by steam reforming on site, excess heat is available at high temperature and in an integrated plant due to the hydrogenation reaction of the ester being a highly exothermic process. Therefore, the overall process is highly energy efficient. In addition, none of the carbohydrate raw material is wasted as $CO_2$ with the attendant generation of heat, which must be wasted to cooling water.

Another advantage of the current invention is the ability to convert natural gas via hydrogen to a liquid product, e.g., ethanol, at very high yield. This feature can be utilized in situations where any carbohydrate source is located close to a source of natural gas production or easy transportation by pipeline. This allows the utilization of gas in remote geographies, such as islands that produce both gas and sugar cane or other carbohydrate crop, to produce an easily transported liquid chemical or fuel, again at high efficiency. For example, plant using the process of the present invention could be located on the island of Trinidad, where natural gas and carbohydrate sources are available at economically attractive prices. The plant can produce substantially pure ethanol for transport in liquid form to a remote location where it can be economically utilized, such as the Texas Gulf Coast. The ethanol can be used as a fuel or a feedstock for further processing. For example, the ethanol can be converted to ethylene and sold through existing ethylene pipeline systems. Alternatively, the ethanol can be recycled within the plant for production of ethyl acetate. In other words, the plant can be used to produce a liquid product comprising substantially all ethyl acetate, substantially all ethanol or any combination of the two. Because the natural gas and carbohydrate source are located relatively close to each other, these feedstocks can be converted to a higher value liquid product which can be easily transported to a remote location in an economic manner.

Preferably, the carbohydrate source and the natural gas source are located within five hundred miles of each other, more preferably within three hundred miles of each other and more preferably within two hundred miles of each other. Preferably, the remote location to which the transportable liquid product is located where economic transportation of the carbohydrate and natural gas is not viable, e.g., more than eight hundred miles, more preferably more than a thousand miles and more preferably more than fifteen hundred miles from the point of production. It will be appreciated that it is generally easier to transport the carbohydrate source to the source of the natural gas. It will also be appreciated that the specific distances that favor an economic advantage will vary depending on the price of the feedstocks, the price of the transportable liquid product and transportation costs. As will be appreciated by one skilled in the art, transportation costs are influenced by a number of factors, including geographic barriers, such a mountain ranges, bodies of water, etc. and are not solely dependent on distances. As a further example, natural gas and carbohydrate sources can be found in Australia and/or New Zealand. A plant located on these island nations could produce ethanol and/or ethyl acetate for transport to Asia, and in particular, Japan, Taiwan, Korea and China.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method comprising:
   a. culturing a microorganism to produce a dilute solution of a carboxylic acid salt, the cation of which is capable of producing an insoluble salt when combined with a weak acid;
   b. acidifying the dilute carboxylic acid salt solution with a weak acid to produce a carboxylic acid and an insoluble salt of the cation and the weak acid;
   c. esterifying the carboxylic acid with alcohol to form an ester; and
   d. recovering the ester.

2. The method of claim 1, wherein the microorganism is cultured in fermentation medium comprising biomass.

3. The method of claim 2, wherein the biomass is selected from the group consisting of grass, trees, wood, paper, corn, rice, manure, crop residue, agricultural waste, and municipal waste.

4. The method of claim 3, wherein prior to fermentation, the biomass is treated using at least one treatment selected from the group consisting of heating and enzymatic hydrolysis.

5. The method of claim 1, wherein the microorganism is cultured using a fermentation medium that comprises carbohydrate.

6. The method of claim 5, wherein at least 60% of the carbon in the carbohydrate is converted into the ester.

7. The method of claim 1, wherein the carboxylic acid is selected from the group consisting of lactic acid and acetic acid.

8. The method of claim 1, wherein the cation is calcium.

9. The method of claim 1, wherein the weak acid is $CO_2$.

10. The method of claim 1, wherein the insoluble salt is a carbonate salt.

11. The method of claim 1, wherein the insoluble salt is calcium carbonate.

12. The method of claim 1, wherein the step of culturing comprises:
   (i) producing lactic acid, lactate, or mixtures thereof, by fermentation; and
   (ii) converting the lactic acid, lactate, or mixtures thereof, into acetic acid, acetate or mixtures thereof.

13. The method of claim 12, wherein the lactic acid is converted into acetic acid by fermentation.

14. The method of claim 1, wherein the step of culturing comprises using at least one homofermentative organism.

15. The method of claim 1, wherein the step of culturing comprises using at least one homoacetogenic organism.

16. The method of claim 1, wherein the step of culturing uses at least one organism from a genus selected from the group consisting of *Lactobacillus, Clostridium, Acetobacterium*, and *Peptostreptococcus*.

17. The method of claim 1, wherein the step of culturing uses at least one organism selected from the group consisting of *Lactobacillus casei, Clostridium formicoaceticum*, and *Clostridium thermoaceticum*.

18. The method of claim 1, wherein the alcohol is selected from the group consisting of methanol and ethanol.

19. The method of claim 1, further comprising hydrogenating the ester to produce alcohol.

20. The method of claim 19, wherein the hydrogen used for hydrogenation is produced by steam reforming.

* * * * *